United States Patent [19]

Barr et al.

[11] Patent Number: 5,133,891

[45] Date of Patent: Jul. 28, 1992

[54] TREATMENT OF PLANTS FOR FROST PROTECTION

[75] Inventors: Garland G. Barr, El Campo, Tex.; Richard Hanrahan, Raleigh, N.C.

[73] Assignee: Rhone Poulenc AG Co., Research Triangle Park, N.C.

[21] Appl. No.: 515,101

[22] Filed: Apr. 27, 1990

[51] Int. Cl.$^5$ ............................................. C09K 3/18
[52] U.S. Cl. ...................................... 252/70; 106/13; 47/2
[58] Field of Search ................. 252/70; 47/2; 106/13

[56] References Cited

U.S. PATENT DOCUMENTS

| | | | |
|---|---|---|---|
| 2,773,796 | 12/1956 | Hackmann et al. | 424/605 |
| 2,824,113 | 2/1958 | Zech | 260/413 |
| 3,129,529 | 4/1964 | Rumsey et al. | 252/70 |
| 3,308,161 | 3/1967 | Shen | 564/463 |
| 3,591,682 | 7/1971 | Thiolliere | 514/114 |
| 3,756,956 | 9/1973 | Panusch | 252/70 |
| 3,879,188 | 4/1975 | Fritz et al. | 47/2 |
| 4,075,324 | 2/1978 | Thizy et al. | 424/601 |
| 4,139,616 | 2/1979 | Ducret et al. | 514/141 |
| 4,143,144 | 3/1979 | Tobol et al. | 546/269 |
| 4,219,965 | 9/1980 | Freebairn et al. | 47/2 |
| 4,382,928 | 5/1983 | Abblard et al. | 514/114 |
| 4,542,023 | 9/1985 | Lacroix et al. | 514/126 |
| 4,618,442 | 10/1986 | Geary et al. | 47/2 |
| 4,834,899 | 5/1989 | Klevecz | 252/70 |

FOREIGN PATENT DOCUMENTS

| | | |
|---|---|---|
| 747351 | 9/1970 | Belgium . |
| 747352 | 9/1970 | Belgium . |
| 249566 | 12/1987 | European Pat. Off. . |
| 806535 | 12/1958 | United Kingdom . |
| 21636523 | 3/1986 | United Kingdom ................. 514/75 |

OTHER PUBLICATIONS

*Ice Nucleating Bacteria*, Genie Rural, pp. 19–23, Nov. 1986.
Chem. Abstracts, 86:166380z, vol. 86, 1977.
Henri Boue, Le Feu Bacterieu des Pomoidees, Phytoma, pp. 27–29, Sep.–Oct. 1984.

*Primary Examiner*—Paul Lieberman
*Assistant Examiner*—Christine A. Skane
*Attorney, Agent, or Firm*—Morgan & Finnegan

[57] ABSTRACT

The present invention is a method of treatment of plants for frost protection. In this method the plants are treated with 1 to 5 kg/ha of an active material of the formula $$[R-O-PH(=O)-O-]_n M^{n+}.$$

17 Claims, No Drawings

TREATMENT OF PLANTS FOR FROST PROTECTION

BACKGROUND OF THE INVENTION

1. Field of the Invention

The instant invention is related to a method of treatment of plants for frost protection.

2. Discussion of Background

It is well known that frost is able to severely damage many kinds of crops. However, the fact is that in cold or temperature climatic zones, frosts frequently occur so that farmers take into account this risk as a matter of routine, and hence crops which are most sensitive to frost are not cultivated. This consequent is that the crops where the frost risk is the highest are in or near semi tropical areas. Citrus is an example of such a crop. Frosts occur infrequently in citrus growing areas and thus the majority of growers are not equipped to deal with the problem. When frosts occur therefore the losses can be considerable. Even if such a situation happens only once every 5 to 10 years, the damage can be catastrophic due to the fact that a complete citrus orchard can be destroyed.

As a consequence, it is highly desirable to have some means of protecting plants and/or crops and/or orchards against frost.

SUMMARY OF THE INVENTION

An object of this invention is to provide a method of treatment of plants for frost protection.

Another object of this invention is to provide a method of treatment of orchards against frost attack.

Another object of this invention is to provide a method of treatment of citrus trees and orchards for frost protection.

Another object of this invention is to provide a method of treatment of plants for frost protection which uses a chemical compounds.

Another object of this invention is to provide a method of treatment of plants for frost protection which is not phytotoxic to treated plants.

Another object of this invention is to provide a method of treatment of plants against bacteria which are non phytopathogenic but which induce the formation and development of ice crystals.

It has now been found that these objectives can be reached by the process of the present invention.

The invention is a method of treatment of plants, especially of citrus trees and/or orchards, which are under actual or potential frost attack characterized by the fact that the plants are treated with 1 to 5 kg/ha (preferably 2 to 4 kg/ha) of an active material of formula

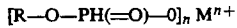

wherein
- R is a hydrogen atom or an alkyl radical of 1 to 4 carbon atoms,
- M is a hydrogen atom, an alkali atom, alkaline earth atom, or aluminum metal atom, and
- n is an integer which is equal to the valence of M.

DETAILED DESCRIPTION OF THE INVENTION

It has been recently discovered that frost damage is increased by the action of certain bacteria which help ice crystal formation and development. Such bacteria are normally not phytotoxic or phytopathogenic, so that no information can be obtained from the existing means of control of phytotoxic or phytopathogenic bacteria diseases.

A further problem is that it is very difficult to learn anything about the control of bacteria under field conditions because field experimentation of bacteria is sometimes regulated and forbidden.

Examples of crops which are affected by frost attack are citrus, including orange trees, grapefruit trees and lemon trees.

It is now been found that these objectives can be reached by the process of the present invention.

The invention is a method of treatment of plants, especially of citrus trees and/or orchards, which are under actual or potential frost attack characterized by the fact that the plants are treated with a 1 to 5 kg/ha (preferably 2 to 4 kg/ha) of an active material of formula

wherein
- R is a hydrogen atom or an alkyl radical of 1 to 4 carbon atoms,
- M is a hydrogen atom, an alkali atom, alkaline earth atom, or aluminum metal atom, and
- n is an integer which is equal to the valence of M.

According to a preferred feature of the invention, the plants treated are citrus trees and/or orchards. According to a further feature of the invention the treatment of such orchards is made before the frost season, that is to say at the end of autumn or at the beginning of winter. Typically, this time period is from the last month of autumn through the first month of winter. Preferably, the treatment according to the invention is made once, but can be repeated as frequently as desired, especially after rain. If no rain falls, no substantial advantage is obtained by applying many treatments. Protection according to the invention is particularly valuable against frost conditions between 0° and −5° C. (32° and 23° F.) or still lower temperatures.

The treatment is made by spraying the foliar canopy including any flowers that may be present.

The present invention is further illustrated by the following non-limiting examples.

EXAMPLES

An orange fruit orchard was treated once in November. Frost conditions occurred in January. No rainfall occurred between the time of the treatment and the frost time.

The treatment according to the invention was made using aluminum tris-[O-ethyl phosphonate] (designated hereafter as fosetyl-Al) in the form of a wettable powder. The concentration of fosetyl-Al in the spray suspension was 4500 ppm, which corresponds to an application rate of 4.5 kg/ha of active ingredient. After treatment the plants were allowed to dry.

To make a comparison, a similar treatment was made with copper hydroxide at the normal rate of 2.24 kg/ha of metallic copper (a higher rate cannot be used because of the phytotoxic effect of the copper hydroxide).

The results obtained are presented in Table 1. The external frost injury on fruits are observed and the results are expressed as the percent reduction of fruit injury.

TABLE 1

| Example | Protective agent | Percent reduction of all injuries | Percent reduction of severe injuries | Percent of reduction of internal injuries of the fruits |
|---|---|---|---|---|
| 1 | fosetyl-Al | 53 | 82 | 50 |
| 2 | Cu(OH)$_2$ | 40 | 64 | 100 |

While specific embodiments of the method aspects of the invention have been shown and described, it should be apparent that many modifications can be made thereto without departing from the spirit and scope of the invention. Accordingly, the invention is not limited by the foregoing description, but is only limited by the scope of the claims appended hereto.

We claim:

1. A process of protecting frost sensitive plants against frost injury, said process comprising the steps of:
   a) applying to said plants, during a period of actual or potential frost attack resulting from frost-producing temperatures between about 0° C. and −5° C., an effective amount of an active material of a formula $$[R-O-PH(=O)-O^-]_n M^{n+}$$

wherein:
   R is a hydrogen atom or an alkyl radial of 1 to 4 carbon atoms;
   M is a hydrogen atom, an alkali atom, alkaline earth atom, or aluminum metal atom; and
   n is an integer which is equal to the valence of M, optionally, the different M are different when n is greater than 1; and
   b) reducing frost injury to said plants, said injury resulting from bacterially induced ice crystal formation and development on said plants during frost producing temperatures.

2. The process according to claim 1, wherein the effective amount of the active material is applied at a rate of 1 to 5 kg/ha.

3. The method according to claim 2, wherein the active material is applied at a rate from 2 to 4 kg/ha.

4. The method according to claim 1, wherein the plants are citrus trees.

5. The method according to claim 3, wherein the plants are citrus trees.

6. The method according to claim 1, wherein the plants are citrus orchards.

7. The method according to claim 3, wherein the plants are citrus orchards.

8. The method according to claim 1, wherein the treatment is made before the frost season.

9. The method according to claim 5, wherein the treatment is made before the frost season.

10. The method according to claim 7, wherein the treatment is made before the frost season.

11. The method according to claim 1, wherein the treatment is made at the end of autumn or at the beginning of winter.

12. The method according to claim 10, wherein the treatment is made at the end of autumn or at the beginning of winter.

13. The method according to claim 8, wherein the treatment is made once and optionally repeated after rain.

14. The method according to claim 11, wherein the treatment is made once and optionally repeated after rain.

15. The method according to claim 1, wherein the treatment is made by spraying the foliar canopy including any flowers that may be present.

16. The method according to claim 14, wherein the treatment is made by spraying the foliar canopy including any flowers that may be present.

17. The method according to claim 1, wherein the material comprises aluminum tris-[O-ethyl phosphonate].

* * * * *